(12) United States Patent
Holmqvist et al.

(10) Patent No.: US 9,750,889 B2
(45) Date of Patent: Sep. 5, 2017

(54) DEVICE FOR MEDICAMENT DELIVERY WITH SYRINGE-LIKE USABILITY HAVING A RESTRAINING MECHANISM

(75) Inventors: Anders Holmqvist, Värmdö (SE); Maria Hedin, Solna (SE)

(73) Assignee: SHL Group AB, Nacka Strand (SE)

( * ) Notice: Subject to any disclaimer, the term of this patent is extended or adjusted under 35 U.S.C. 154(b) by 123 days.

(21) Appl. No.: 14/118,318

(22) PCT Filed: May 7, 2012

(86) PCT No.: PCT/SE2012/050477
§ 371 (c)(1),
(2), (4) Date: Dec. 12, 2013

(87) PCT Pub. No.: WO2012/158095
PCT Pub. Date: Nov. 22, 2012

(65) Prior Publication Data
US 2014/0316334 A1   Oct. 23, 2014

Related U.S. Application Data

(60) Provisional application No. 61/487,792, filed on May 19, 2011.

(30) Foreign Application Priority Data

May 19, 2011 (SE) ....................... 1150466

(51) Int. Cl.
*A61M 5/315* (2006.01)
*A61M 5/28* (2006.01)

(52) U.S. Cl.
CPC ........ *A61M 5/31571* (2013.01); *A61M 5/284* (2013.01); *A61M 5/31595* (2013.01);
(Continued)

(58) Field of Classification Search
CPC .......... A61M 5/31525; A61M 5/31501; A61M 5/315; A61M 5/31526; A61M 5/31528;
(Continued)

(56) References Cited

U.S. PATENT DOCUMENTS 1,393,720 A    10/1921   Lomas et al.
2,502,639 A *   4/1950   Blake ........................... 604/210
(Continued)

FOREIGN PATENT DOCUMENTS

DE         1006589 B     4/1957
GB          107833 A     7/1917
(Continued)

OTHER PUBLICATIONS

EPO, Int'l Search Report in PCT/SE2012/050477, Oct. 24, 2012.
EPO, Written Opinion in PCT/SE2012/050477, Oct. 24, 2012.

*Primary Examiner* — Imani Hayman
*Assistant Examiner* — Nilay Shah
(74) *Attorney, Agent, or Firm* — Piedmont Intellectual Property (57) ABSTRACT

Device for medicament delivery with syringe-like usability having a restraining mechanism A device for medicament delivery with syringe-like usability comprising at least one grip, at least one medicament container holder, and at least one plunger rod being substantially rotationally fixed relatively to the grip. The medicament container holder (13) is movable towards the grip in a longitudinal direction of the device, and rotation of at least one rotatable part (40), which is rotatable relatively to the grip and substantially inhibits movement of the plunger rod (20) in a longitudinal direction for dose delivery when in at least one locking position until being rotated, is restrained by at least one restraining member (42) abutting or being connected to the rotatable part (40) and the grip (30) until the medicament container holder
(Continued)

is moved towards the grip for interacting with the at least one restraining member.

18 Claims, 5 Drawing Sheets

(52) U.S. Cl.
CPC .......... *A61M 5/315* (2013.01); *A61M 5/3156* (2013.01); *A61M 5/3157* (2013.01); *A61M 5/31501* (2013.01); *A61M 5/31525* (2013.01); *A61M 5/31526* (2013.01); *A61M 2005/3154* (2013.01)

(58) Field of Classification Search
CPC .......... A61M 5/31535; A61M 5/31536; A61M 2005/3154; A61M 5/31593; A61M 5/31596; A61M 5/3135; A61M 5/3137; A61M 5/3148; A61M 5/31505; A61M 2005/31508; A61M 5/3155; A61M 5/3156; A61M 5/31585
See application file for complete search history.

(56) References Cited

U.S. PATENT DOCUMENTS

| | | | |
|---|---|---|---|
| 2,648,334 A | | 8/1953 | Brown et al. |
| 2,707,954 A | * | 5/1955 | Kas, Sr. .................. A61M 5/24 604/210 |
| 4,050,459 A | * | 9/1977 | Sanchez ........................ 604/210 |
| 4,973,318 A | * | 11/1990 | Holm ...................... A61M 5/24 604/208 |
| 5,318,544 A | | 6/1994 | Drypen et al. |
| 5,785,682 A | * | 7/1998 | Grabenkort ..................... 604/82 |

FOREIGN PATENT DOCUMENTS

| | | |
|---|---|---|
| WO | 2009/095735 A1 | 8/2009 |
| WO | 2012/158096 A1 | 11/2012 |

* cited by examiner

DEVICE FOR MEDICAMENT DELIVERY WITH SYRINGE-LIKE USABILITY HAVING A RESTRAINING MECHANISM

TECHNICAL FIELD

The present invention relates to a medicament delivery device with syringe-like usability having a restraining mechanism that restrains a rotatable part of a locking mechanism until the device is ready for use. More specifically, the present invention relates to a medicament delivery device with syringe-like usability having a restraining member that restrains rotation of a rotatable part of a locking mechanism until a medicament container and/or a medicament container holder is moved relatively to a grip of the device. The locking mechanism may be a mechanism which allows for intermittent injection of defined doses of medicament.

RELATED ART

Traditionally with a conventional hypodermic syringe a practitioner or user can inject a medicament by depressing a plunger along the longitudinal axis of the syringe. The injected volume typically is determined from a scale on the hypodermic syringe and the practitioner has to stop depressing the plunger relying on visual feedback. Consequently, it is difficult to perform a repeated dose injection with a high degree of accuracy and/or precision and inadequate doses may be injected, for example, when human errors occur.

U.S. Pat. No. 5,318,544 discloses a syringe for metering precise volumes of fluid. The syringe comprises a plunger with a plurality of stop surfaces which contact a stop on a syringe tube. The stop surfaces are linearly offset from each other along and angularly displaced about a longitudinal axis of the plunger by distances corresponding to predetermined volumes of fluid to be metered. Thereby, incremental rotation of the plunger permits successive stop surfaces to limit the motion of the plunger and thus allows metering of predetermined fluid volumes.

However, having to turn the plunger rod may result unusual and irritating to practitioners or users that are accustomed to depress the plunger rod in a linear manner. For this reason, many practitioners prefer devices which allow intermittent injection of defined doses but do not require turning the plunger, i.e., devices having a syringe-like usability. Furthermore, the syringe disclosed in U.S. Pat. No. 5,318,544 does not provide an indication on whether the device is ready to use. This may be confusing to the practitioner or user.

WO 2009/095735 discloses a device having a plunger that is depressed to expel a dose. Features on the plunger and features connected to the barrel interact to provide for intermittent stops to the injection process. Although the plunger of WO 2009/095735 may be depressed in a linear manner, the device lacks means for clearly indicating whether the device is ready to use. Furthermore, the mechanism of the device increases the diameter of the device substantially. The device also lacks a mechanism that prevents the device from being used before certain preparation steps have been carried out and the device is ready.

There is, therefore, a need for devices for medicament delivery that allow expelling repeated doses in a precise, easy, ergonomic and controlled manner but are easy to use because they have a syringe-like usability. In particular, there is a need for devices having a syringe-like usability that clearly indicate the enablement or disablement of the device each time a user aims to eject a predetermined volume of medicament. Since the presently known mechanisms providing some of these features enlarge the device as a whole, there is also a need for mechanisms that require less space but can still be used easily, ergonomically and safely as well as devices featuring such mechanisms.

Furthermore, it is desirable for the respective mechanisms to be blocked until the necessary preparation steps have been carried out and the device is ready for use. For example, the mechanisms should be blocked until the device is primed. Thus, there is also a need for devices being safe or safer against accidental actuation and for devices that ensure that certain and/or all necessary priming steps are carried out before the device can be used and a dose can be delivered.

SUMMARY OF THE INVENTION

In order to overcome one or several of the above-mentioned problems and achieve the above-mentioned objectives, medicament delivery devices according to the independent claims are provided.

Further aspects, improvements and variations are disclosed in the dependent claims, the figures and the description.

In the present application, when the term "distal" is used, this refers to the direction pointing away from the dose delivery site. When the term "distal part/end" is used, this refers to the part/end of the delivery device, or the parts/ends of the members thereof, which is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which is/are located closest to the dose delivery site.

The device for medicament delivery of the present invention allows injecting doses in an intermittent manner. The device preferably allows intermittent injection of defined doses from a single medicament container. The dose injection, which preferably is carried out by a practitioner or user actuating the device by pushing the plunger rod, is precise, easy and controlled.

The device for medicament delivery of the present invention comprises at least one locking mechanism and at least one plunger rod. The locking mechanism is configured to substantially inhibit dose delivery when being in at least one locking position. Preferably, when being in a locking position, the locking mechanism is configured to substantially inhibit movement of at least one plunger rod relative to other parts of the device. For example, the locking mechanism may be configured to substantially inhibit movement of the plunger rod relative to at least one part of at least one grip of the device and/or relative to at least one medicament container when being in a locking position. Preferably, the locking mechanism is configured to substantially inhibit movement of the plunger rod in a proximal direction when being in a locking position. More preferably, the locking mechanism is configured to substantially inhibit movement of the plunger rod in a proximal direction along the longitudinal axis of the device when being in a locking position.

Preferably, the locking mechanism is configured to allow dose delivery when being in at least one delivery position. When being in the delivery position, the locking mechanism preferably is configured to allow dose delivery by injection. Preferably, when being in a delivery position, the locking mechanism is configured to allow at least a certain movement of at least one plunger rod relative to other parts of the device. For example, the locking mechanism may be configured to allow at least a certain movement of the plunger rod relatively to at least one part of at least one grip of the device and/or relatively to at least one medicament container when being in a delivery position. When being in a delivery position, the locking mechanism preferably is configured to allow at least a certain movement of the plunger rod in a proximal direction, more preferably, to allow a certain movement of the plunger rod in the proximal direction along the longitudinal axis of the device.

Moving the plunger rod in the proximal direction preferably leads to at least one medicament being expelled from at least one medicament container. The medicament preferably is in a liquid state and the medicament container preferably is positioned in a medicament container holder. Preferably, the medicament is expelled from the medicament container by the plunger rod pushing a plunger positioned in the container. The medicament preferably is injected through a delivery member. Preferably, a needle is used to inject the medicament to a patient or animal. The needle preferably is positioned at the proximal end of the device.

When being in a locking position and/or when being in a delivery position, the locking mechanism may substantially inhibit movement of the plunger rod in the distal direction. More preferably, the locking mechanism substantially inhibits movement of the plunger rod in the distal direction when being in a locking position and when being in a delivery position.

The device for medicament delivery of the present invention preferably comprises a mechanism that prevents the locking mechanism from being actuated, i.e. from being set in a delivery position, before the device is ready for use. Preferably, this functionality is provided by the locking mechanism itself and does not require further mechanisms therefore. For example, the locking mechanism may be configured such that actuation of the locking mechanism is prevented before the device is primed or before a delivery member is connected to the device. Priming the device leads to deair at least one medicament container or at least one dual chamber medicament container after its contents have been mixed.

Rotatable Part

The locking mechanism of the device for medicament delivery of the present invention comprises at least one rotatable part and at least one indicator drum, the rotatable part being configured to substantially inhibit longitudinal movement of at least one plunger rod when the locking mechanism is in a locking position. The rotatable part preferably is configured to substantially inhibit longitudinal movement of the plunger rod when the locking mechanism is in a locking position by interacting with the plunger rod. This may be achieved by providing the rotatable part with at least one projection, rib or block. The projection, rib or block of the rotatable part may interact and/or be in engagement with at least one channel and/or at least one projection, rib or block of the plunger rod. Preferably, the rotatable part interacts and/or is engaged with the plunger rod directly.

The rotatable part preferably has a generally cylindrical shape or the general shape of a hollow cylinder. Preferably, the rotatable part comprises at least one first projection extending from the wall of the rotatable part in a direction which is substantially perpendicular to the longitudinal axis of the rotatable part. The projection may extend in a radial direction of the rotatable part. Preferably, the rotatable part has the general shape of a hollow cylinder and the at least one first projection extends radially inwards. The projection may have the shape of the segment of a circle.

The device for medicament delivery of the present invention preferably comprises at least one grip. Preferably, the rotatable part can rotate relatively to the grip and is fixed in a longitudinal direction.

The rotatable part may comprise at least one first slot, recess or indent, which may be used to engage further components of the device with the rotatable part. The slot may be a slot in the wall portion of the rotatable part. However, the rotatable part may also comprise at least one second projection instead of said slot. If so, the at least one second projection preferably extends radially outwards from the wall of the hollow cylinder.

Furthermore, the rotatable part may comprise an arm. The arm may be flexible and may interact or be engaged with a recess or slot in the grip to prevent the locking mechanism from being actuated before the device is primed.

The rotatable part may be a rotatable nut.

Plunger Rod

The plunger rod of a device for medicament delivery of the present invention preferably has a plurality of steps provided in a threaded manner along the longitudinal axis of the plunger rod. The plunger rod may thus comprise a plurality of angularly and longitudinally offset abutment surfaces being substantially perpendicular to the longitudinal axis of the plunger rod. The plurality of steps may be formed by a substantially continuous channel comprising grooves orientated along the longitudinal axis of the device and perpendicular thereto. Preferably, a longitudinal groove alternates with a perpendicular one.

The plurality of steps may also be formed by a plurality of projections, ribs or blocks. The plurality of steps may form one substantially continuous projection comprising projections or ribs along the longitudinal axis and projections or ribs perpendicular thereto. However, the steps may also be formed by single, longitudinally and angularly offset blocks. In general, any suitable combination of grooves and projections may be used.

Furthermore, the surface of the plunger rod preferably comprises detents. More preferably, the detents are provided in the channel of the plunger rod. Most preferably, the detents are provided along the grooves of the channel which are orientated perpendicularly to the longitudinal axis of the plunger rod.

Preferably, the plunger rod is configured to be rotationally fixed movable in a longitudinal direction relatively to the at least one grip of the device. For this purpose, the plunger rod may comprise at least one notch along the longitudinal axis and/or at least one projection which interacts or is engaged with at least one projection and/or at least one slot or recess of the grip. Alternatively or additionally, rotation of the plunger rod may be inhibited by the plunger rod having a non-circular cross section. For example, the plunger rod may have a slightly oval cross-section. Most preferably, the plunger rod comprises two longitudinal notches disposed on circumferentially opposite sides of the plunger rod. The device for medicament delivery of the present invention preferably is configured to deliver a dose, i.e., to be actuated, by moving at least one plunger connected to the plunger rod in the proximal direction. Therefore, when the device is the plunger rod preferably is moved relatively to the grip, the rotatable part and the medicament container.

Interaction of the Rotatable Part with the Plunger Rod

The rotatable part preferably is substantially concentric with the plunger rod. Preferably, at least one projection of the rotatable part interacts or is in engagement with the steps on the plunger rod formed by grooves and/or projections and/or blocks. The steps preferably provide longitudinally and angularly offset abutment surfaces, edges or points in a threaded manner. Preferably, the rotatable part comprises at least one projection which interacts or is in engagement with at least one channel of the plunger rod providing said steps.

Initially, preferably at least one abutment contact is formed by a proximally facing surface or edge of the plunger rod abutting against at least one projection of the rotatable part, thereby substantially inhibiting the plunger rod from being moved in the proximal direction. Thus, the locking mechanism is in a locking position.

The abutment contact may be provided by an abutment surface of the plunger rod which is substantially perpendicular to the longitudinal axis of the plunger rod abutting against a projection of the rotatable part. However, it will be clear to the person skilled in the art that also abutment points or lines may be provided, for example, if at least one of the projections has a cylindrical shape.

When being in a locking position, the rotatable part preferably may be rotated a predetermined angle, for example an angle of 90 degrees, until a projection of the rotatable part abuts against at least one further abutment surface or edge of the plunger rod. Thus, rotation of the rotatable part preferably is substantially inhibited when the rotatable part has been rotated for the predetermined angle. For example, an abutment contact may be formed by an abutment surface of the plunger rod, which is substantially parallel to the longitudinal axis of the plunger rod, abutting against a projection of the rotatable part.

When further rotation of the rotatable part is substantially inhibited, the projection or projections of the rotatable part preferably do not inhibit the plunger rod from being moved in the proximal direction anymore. This means that the rotatable part preferably allows the plunger rod to be moved in the proximal direction. Thus, the locking mechanism is in a delivery position, i.e., released from locking. Accordingly, the locking mechanism preferably may be set into a delivery position by rotating the rotatable part relatively to the plunger rod. Once rotated, the rotatable part preferably is substantially inhibited from rotating backwards by detents provided to the plunger rod.

When the locking mechanism is in a delivery position, a dose preferably may be delivered by pushing the plunger rod in the proximal direction. Preferably, the plunger rod may be moved in the proximal direction until another abutment surface or edge of the plunger rod abuts against at least one projection of the rotatable part, thereby substantially inhibiting the plunger rod from being moved in the proximal direction further. For example, an abutment surface of the plunger rod, which is substantially perpendicular to the longitudinal axis of the plunger rod, may abut against a projection of the rotatable part. Thus, the movement of the plunger rod is inhibited once a predetermined dose has been delivered. The locking mechanism is in a locking position again.

When the locking mechanism is in the locking position again after a defined dose has been delivered, preferably at least one protrusion of the rotatable part abuts against at least one groove of the plunger rod. However, as described above, also at least one projection of the rotatable part may abut against at least one protrusion or block of the plunger rod.

Preferably, the locking mechanism can be set to the delivery position, i.e., released from locking, again by rotating the rotatable part further, for example for another angle of 90 degrees, and the next dose can be delivered by moving the plunger rod subsequently. Accordingly, multiple defined doses may be injected in an intermittent manner by iterating the steps described above.

Turning Knob

The device for medicament delivery of the present invention may comprise at least one turning knob. Preferably, the turning knob has a generally cylindrical shape or the general shape of a hollow cylinder. The turning knob preferably is concentric with the plunger rod and/or the rotatable part. More preferably, the rotatable part is arranged concentrically around the plunger rod and the turning knob is arranged concentrically around the rotatable part. The turning knob preferably is held by the grip of the device such that it can rotate relatively to the grip and is fixed in a longitudinal direction.

The turning knob preferably comprises at least one first projection, rib or block that interacts or is in engagement with the at least one first slot of the rotatable part. Preferably, the first projection of the turning knob extends radially inwards into the first slot of the rotatable part. However, when the rotatable part comprises a second projection instead of said first slot, the turning knob may also have at least one recess engaged with the second projection of the rotatable part. The turning knob preferably interacts or is engaged with the rotatable part directly.

Due to their interaction or engagement with each other, the rotatable part and the turning knob preferably rotate integrally. This means that the rotatable part is rotated when the turning knob is turned and that turning of the turning knob is substantially inhibited when the rotatable part is rotationally fixed. Accordingly, when the device comprises a turning knob, the locking mechanism preferably may be set into the delivery position by turning the turning knob and thereby rotating the rotatable part relatively to the plunger rod.

The turning knob preferably comprises at least one second projection, rib or block that interacts or is in engagement with the indicator drum as will be described below. However, it is also considered that a single projection interacts with both, the rotatable part and the indicator drum. Preferably, the turning knob comprises at least one window or transparent segment through which at least one colour field of the indicator drum can be seen.

Indicator Drum

The device for medicament delivery of the present invention comprises at least one indicator drum. The indicator drum preferably has the generally cylindrical shape. More preferably, the indicator drum has a general shape of a hollow cylinder. The indicator drum preferably is substantially concentric with the plunger rod and/or the rotatable part and/or the turning knob. The indicator drum preferably is arranged substantially concentrically around the rotatable part and/or the turning knob is arranged substantially concentrically around the indicator drum. This means that the indicator drum preferably is disposed between the rotatable part and the turning knob.

The indicator drum preferably features at least one colour field configured to indicate if the locking mechanism is in a locking or in a delivery position. More preferably, the at least one colour field is provided on the outer wall of the indicator drum. For example, the colour field may be provided on the outer wall of the hollow cylinder. Most preferably, two colour fields are provided. For example, a red field may be used to indicate that the locking mechanism is in a locking position while a green field may be used to indicate that the locking mechanism is in a delivery position.

The indicator drum may comprise at least one opening. Preferably, the at least one arm of the rotatable part extends through said opening.

The indicator drum of the device for medicament delivery of the present invention preferably interacts or is in engagement with the turning knob and/or the rotatable part. More preferably, the indicator drum interacts or is in engagement with the turning knob and/or the rotatable part over at least one resilient member. Most preferably, one end of the resilient member is connected to the turning knob and/or the rotatable part while the other end of the resilient member is connected to the indicator drum. When the rotatable part and/or the turning knob is rotated, the end of the resilient member connected to the rotatable part and/or the turning knob is preferably rotated therewith.

The resilient member may have any form but preferably has the form of a spiral spring. The resilient member may be integral with the indicator drum and/or the turning knob and/or the rotatable part. Alternatively or additionally, the resilient member may be connected to the indicator drum and/or the turning knob and/or the rotatable part by form closure and/or bonding. Preferably, the resilient member is integral with the indicator drum and connected to the turning knob by form closure. For example, the resilient member may be engaged in the at least one second projection of the turning knob.

Interaction of the Indicator Drum and the Plunger Rod

The indicator drum preferably comprises at least one projection. The at least one projection of the indicator drum preferably interacts with a plurality of steps provided on the plunger rod in a threaded manner along its longitudinal axis. As described above, such steps may be formed by a plurality of angularly and longitudinally offset abutment surfaces being substantially perpendicular to the longitudinal axis of the plunger rod and a plurality of angularly and longitudinally offset abutment surfaces being substantially parallel to the longitudinal axis of the plunger rod. While a first plurality of steps may be provided for the rotatable part and a second plurality of steps may be provided for the indicator drum, preferably both the indicator drum and the rotatable part interact with the same plurality of steps. Thus, the projection of the indicator drum and the rotatable part preferably interact with the same substantially continuous channel formed by a plurality of alternating parallel and perpendicular grooves on the plunger rod.

When the locking mechanism of the device for medicament delivery is in a locking position and/or a delivery position, the projection of the indicator drum preferably substantially inhibits movement of the plunger rod in the distal direction. Preferably, an abutment contact that substantially inhibits movement of the plunger rod in the distal direction is formed by a surface, edge or point of the plunger rod abutting the projection of the indicator drum. More preferably, the abutment contact is formed by an abutment surface of the plunger rod which is substantially perpendicular to the longitudinal axis of the plunger rod abutting against the projection of the indicator drum. It will be clear to the person skilled in the art that also abutment points or lines may be provided, for example, if at least one of the projections has a cylindrical shape. Accordingly, the projection of the indicator drum preferably substantially inhibits the plunger rod being pulled out of the device. The projection of the indicator drum preferably allows movement of the plunger rod in the proximal direction when the locking mechanism of the device is in a locking or a delivery position.

The projection of the indicator drum and the projection the rotatable part interacting with the plunger rod preferably are provided at different positions along the longitudinal axis of the plunger rod and/or at different angles of rotation around the longitudinal axis of the plunger rod.

When the locking mechanism is in a locking position and when the locking mechanism is set to a delivery position by rotating the rotatable part and/or the turning knob, the rotation of the indicator drum preferably is substantially inhibited in a certain direction. Preferably, the rotation of the indicator drum in a certain direction is substantially inhibited by the projection of the indicator drum abutting against at least one further abutment surface or edge of the plunger rod. For example, the projection of the indicator drum may abut against an abutment surface of the plunger rod which is substantially parallel to the longitudinal axis of the plunger rod. The abutment surface may be provided by a groove or a projection of the plunger rod. Therefore, the resilient member connecting the indicator drum with the turning knob and/or the rotatable drum preferably is biased when the turning knob and/or the rotatable part is rotated, i.e., when the locking mechanism is set to the delivery position. Preferably, the indicator drum is substantially inhibited from following the rotation of the rotatable part and/or the turning knob when the device is set to a delivery position by the projection of the indicator drum interacting with and/or abutting the channel of the plunger rod.

Rotating the rotatable part and/or the turning knob relatively to the indicator drum preferably leads to the device indicating that the locking mechanism is set to a delivery position. More preferably, the colour shown by the device is changed. Preferably, the turning knob is positioned over the indicator drum such that the window or the transparent segment of the turning knob is disposed over a certain colour field when the turning knob is rotated relatively to the indicator drum. More preferably, the window or the transparent segment of the turning knob is disposed over a first colour field when the locking mechanism is in a locking position and over a second colour field when the locking mechanism is in a delivery position. However, it will be clear to the person skilled in the art that the colour fields of the indicator drum may also be shown in other ways. For example, the colour field or fields may also be shown through a window of the rotatable drum and/or a window of another component rotating therewith, if the rotatable drum is disposed around the indicator drum. Instead of a window, a transparent field may be used.

Once the device is actuated or once actuation of the device is complete, i.e., when a portion of a dose or the complete dose has been delivered, the indicator drum preferably reset relatively to the turning knob and/or the rotatable part. Preferably, the indicator drum is reset by being rotated in a direction into which rotation was previously inhibited. More preferably, the indicator drum is rotated relatively to the turning knob and/or the rotatable part and the plunger rod.

When the plunger rod is moved in the proximal direction, the projection of the indicator drum preferably does not coincide anymore with the abutment surface, edge or point of the plunger rod against which it was abutting previously. This means that the projection of the indicator preferably slides along a parallel groove until reaching a perpendicular groove when the plunger rod is moved in the proximal direction. Then, the indicator drum preferably slides along the perpendicular groove until reaching the next parallel groove due to the force exerted by the at least one biased resilient member. Accordingly, the indicator drum preferably is rotated when the device is actuated or when actuation of the device is complete. More preferably, the indicator drum is rotated by the force of the at least one biased resilient member a predetermined angle, for example 90 degrees. The device of the present invention is, thus, preferably characterized by the rotation of the indicator drum lagging behind the rotation of the turning knob and/or the rotatable part when the locking mechanism is set to a delivery position and the rotation of the indicator drum following the rotation of the turning knob and/or the rotatable part when a dose is delivered, thereby resetting the position of the indicator drum.

Once rotated, when a dose has been delivered and the locking mechanism is in a locking position again, the indicator drum preferably is inhibited from rotating backwards by the detents of the plunger rod. The indicator drum preferably substantially inhibits movement of the plunger rod in the distal direction as described above again.

Rotating the indicator drum relatively to the turning knob and/or the rotatable part when a dose has been delivered preferably leads to the colour shown through the window of the turning knob and/or the rotatable part being reset. More preferably, the colour field indicating that the locking mechanism is in a locking position is shown again. Most preferably, the red colour field is shown to the user.

Priming

The device for medicament delivery of the present invention preferably comprises a restraining mechanism that prevents the locking mechanism from being actuated, i.e. from being set in a delivery position, before the device is ready for use. The locking mechanism preferably is blocked and/or restrained until the device is primed. Preferably, rotation of the rotatable part and/or the turning knob is substantially inhibited until the device is primed. More preferably, rotation of the rotatable part and/or the turning knob is substantially inhibited and/or restrained until the device is primed by at least one restraining member abutting or being connected to the rotatable part and/or the turning knob abutting or being connected to at least one rotationally fixed member. The restraining member may be an arm of the rotatable part and/or a member connected to the rotatable part, the arm being engaged with at least a part of the grip. The restraining member may interact with a projection or a recess of the grip.

The device for medicament delivery of the present invention preferably is configured to be primed by screwing and/or pushing at least one medicament container and/or at least one medicament container holder into at least one grip. The medicament container or the medicament container holder and the grip may be threaded for this purpose. Initially, the arm of the rotatable part or of a member connected to the rotatable part preferably is engaged in at least one slot provided in the grip.

When the medicament container holder and/or the medicament container is moved towards the grip, for example by screwing and/or pushing the medicament container holder and/or the medicament container into the grip preferably interacts with the at least one restraining member and disengages the restraining member from the rotatable part, a member connected to the rotatable part and/or the grip. Preferably, the arm of the rotatable part is disengaged from the grip so that the rotatable part can be rotated. More preferably, screwing and/or pushing the medicament container holder and/or the medicament container into the grip pushes the arm out of the slot provided in the grip.

Alternatively, other movable parts abutting the rotatable part and the grip may be provided, e.g., a slidable disk having projections and/or recesses that interact with recesses and/or protrusions of the rotatable part and the grip until the disk is moved by screwing and/or pushing the medicament container holder, the medicament container and/or another movable element of the device into the grip.

Furthermore, it will be clear to the person skilled in the art that the restraining mechanism described above may also be implemented in other devices for intermittent injection, e.g., devices having a rotatable plunger rod as disclosed in U.S. Pat. No. 5,318,544. In such devices, the arm could be made integral with the grip and abut a projection of the plunger rod, thus restraining rotation of the plunger rod until the medicament container holder and/or the medicament container is screwed and/or pushed into the grip.

The device for medicament delivery of the present invention may comprise at least one medicament container. The medicament container may be a regular medicament container or a dual chamber medicament container. Priming the device leads to deair at least one medicament container or at least one dual chamber medicament container after its contents have been mixed. In this case the priming thread of the medicament container or the medicament container holder may be longer and configured to move a member in the medicament container in order to adequately deair the container or to adequately mix the contents within a dual chamber container and deair after mixing.

The present invention thus provides a device for medicament delivery having a syringe-like usability and comprising a mechanism that allows intermittent injection of multiple doses in a precise, easy and controlled manner. The mechanism is disposed along the longitudinal axis of the device. Therefore, it requires minimal space and does not substantially enlarge the device as a whole but is still easy to use. The mechanism may also clearly indicate enablement or disablement of the device to a user. Furthermore, the present invention provides devices for medicament delivery that comprise a restraining mechanism which prevents actuation of a mechanism for intermittent injection before the device is ready for use, thus making the use of such devices safer.

While the device has been described with respect to medicament delivery, it will be clear to the person skilled in the art that the inventive device can also be used for intermittently ejecting exact doses of other substances and/or liquids, such as glue.

BRIEF DESCRIPTION OF THE DRAWINGS

The following Figures below disclose an embodiment of the invention for illustrational purposes only. In particular, the disclosure within the Figures is not meant to limit the range of protection of the invention. The embodiment shown may be modified in many ways within the scope of the claims.

DETAILED DESCRIPTION OF THE DRAWINGS

Figure 1:
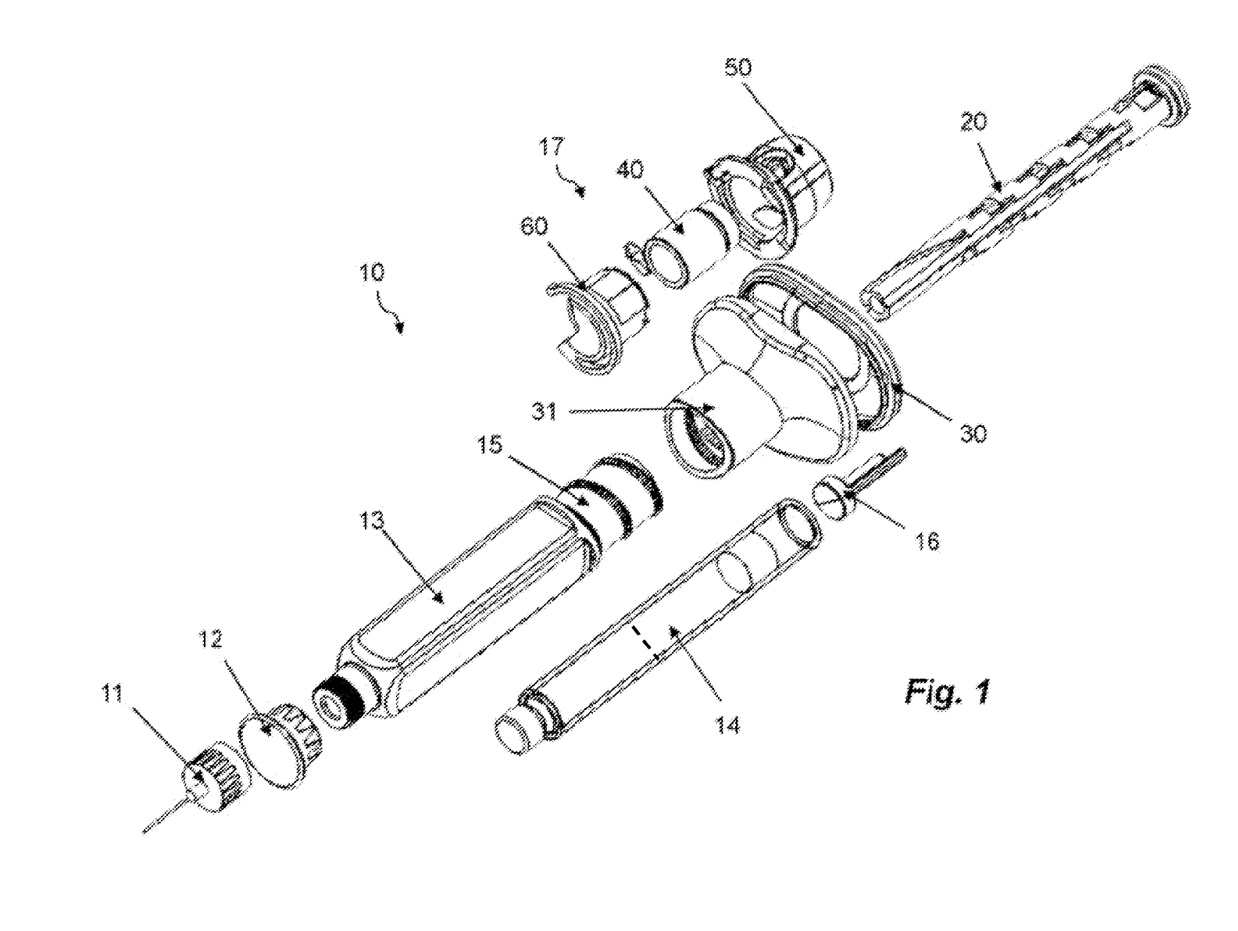
FIG. 1: Exploded view of a device for medicament delivery of the present invention.

FIG. 1 shows an exploded view of a device for medicament delivery 10 according to the present invention. The device 10 comprises a plunger rod 20 and a locking mechanism 17. The locking mechanism 17 includes a rotatable part 40 and an indicator drum 60 and may further comprise a turning knob 50. The device 10 may further have a medicament container holder 13 and a medicament container 14 and a grip. The grip may comprise a distal grip part 30 and a proximal grip part 31. The medicament container holder 13 may comprise a threaded part 15 for screwing the medicament container holder 13 into the proximal grip part 31. A plunger 16 may be disposed in the medicament container 14 and connected to the plunger rod 20. The device may be provided with a hygiene cap 12 which can be exchanged for a needle 11.

Figures 2, 3:
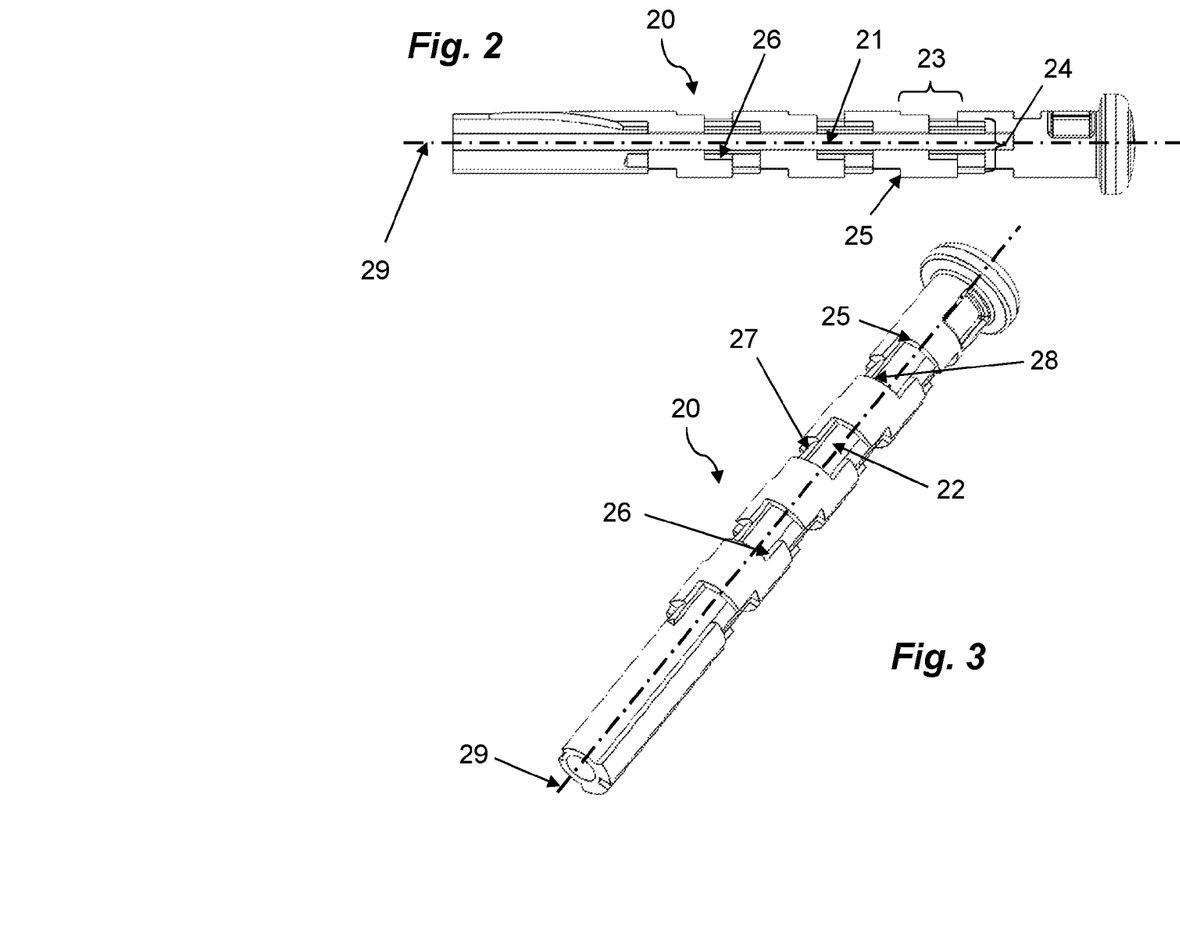
FIG. 2: Plan view showing a plunger rod of a device for medicament delivery according to the present invention.
FIG. 3: Perspective view showing a plunger rod of a device for medicament delivery according to the present invention.
Figure 12:
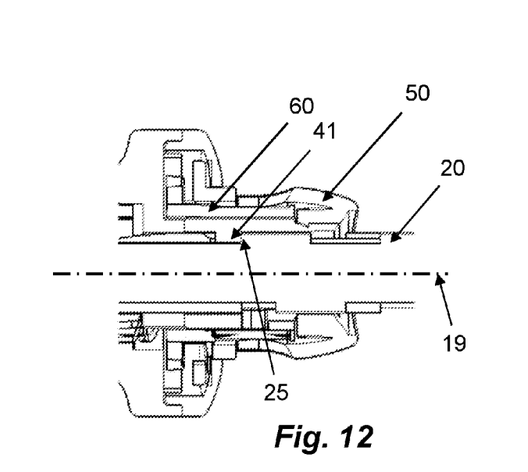
FIG. 12: Sectional view showing the locking mechanism of a device for medicament delivery according to the present invention in the locking position, the sectional plane being parallel to the longitudinal axis of the device.

FIG. 2 shows a plan view of a plunger rod 20 of a device for medicament delivery 10 according to the present invention. The plunger rod 20 may comprise at least one longitudinal notch 21. Preferably, the plunger rod 20 comprises two longitudinal notches 21. The longitudinal axis 29 of the plunger rod 20, visible in FIGS. 2 and 3, preferably corresponds to the longitudinal axis 19 of the device 10 shown in FIGS. 12, 14 and 15, which preferably is equal to the longitudinal axis of the needle 11.

As visible most clearly in FIG. 3, the plunger rod 20 may comprise a plurality of steps provided in a threaded manner along the longitudinal axis 29 of the plunger rod 20. The steps may be formed by a plurality of angularly and longitudinally offset abutment surfaces 25 being substantially perpendicular to the longitudinal axis 29 of the plunger rod 20 and facing towards the proximal end of the plunger rod 20 and a plurality of angularly and longitudinally offset abutment surfaces 26 being substantially parallel to the longitudinal axis 29 of the plunger rod 20. The plurality of steps may also be formed by a substantially continuous channel 22 formed by a plurality of grooves 23, 24. Grooves 23, which are parallel to the longitudinal axis 29 of the plunger rod 20 (parallel grooves 23), and grooves 24, which are perpendicularly to the longitudinal axis 29 of the plunger rod 20 (perpendicular grooves 24), alternate. As it will be clear to the person skilled in the art, the plurality of steps may also be formed by a plurality of projections, ribs or blocks disposed on the plunger rod 20. The plurality of steps may be formed by one substantially continuous projection comprising projections or ribs parallel and perpendicular to the longitudinal axis 29 of the plunger rod. However, the steps may also be formed by single, longitudinally and angularly offset blocks. In general, any suitable combination of grooves, projections and blocks may be used.

The surface of the plunger rod 20 preferably comprises detents 27. More preferably, the detents are provided in the channel 22 of the plunger rod. Most preferably, the detents are provided along the grooves 24 of the channel 22, which are orientated perpendicularly to the longitudinal axis 29 of the plunger rod 20.

Figures 4, 5, 6:
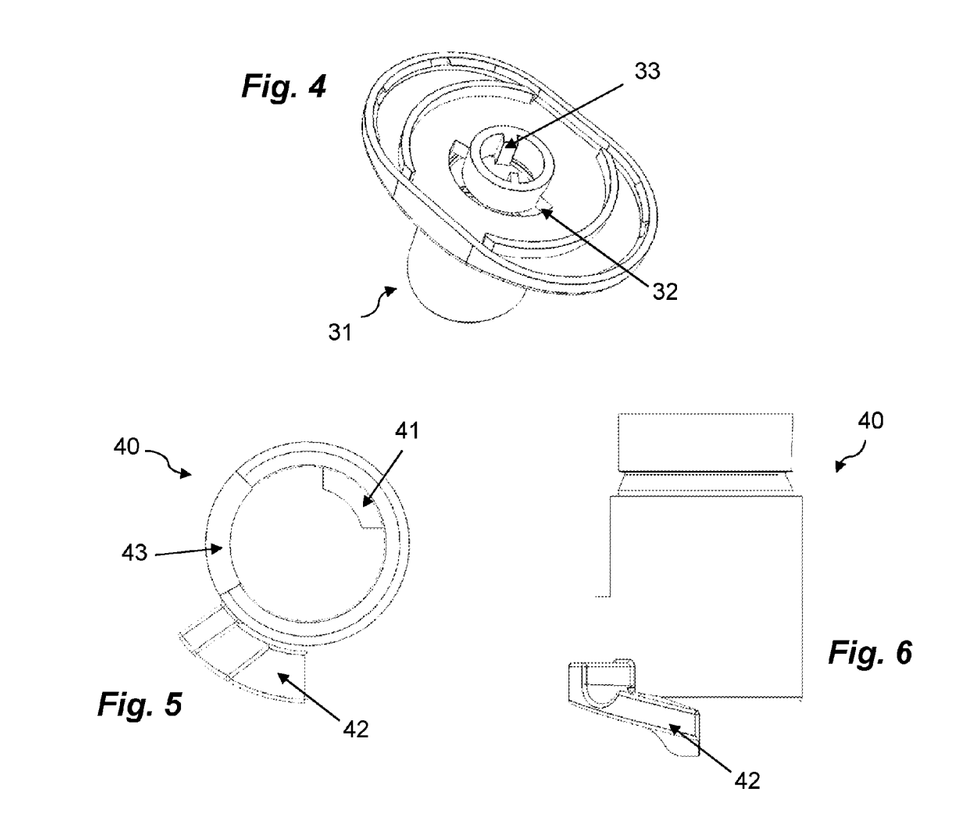
FIG. 4: Perspective view showing the lower grip part of a device for medicament delivery according to the present invention.
FIG. 5: Plan view showing a rotatable part of a device for medicament delivery according to the present invention.
FIG. 6: Side view showing a rotatable part of a device for medicament delivery according to the present invention.

FIG. 4 shows a perspective view of the proximal grip part 31 of a device for medicament delivery 10 according to the present invention. The proximal grip part 31 may comprise a projection 33. The projection 33 of the proximal grip part 31 preferably interacts with the at least one longitudinal notch 21 of the plunger rod 20. Preferably, the proximal grip part 31 comprises two projections 33, each cooperating with one of the longitudinal notches 21. The plunger rod thus preferably can be moved along the longitudinal direction of the device 10, i.e. along the longitudinal axis 19 thereof, but is inhibited from rotating by the grip. The proximal grip part 31 may further comprise at least one recess or slot 32. Instead of a recess 32, a projection may be provided.

FIGS. 5 and 6 show a plan view and a side view of a rotatable part 40 of a device for medicament delivery 10 according to the present invention. The rotatable part 40 preferably has the general shape of a hollow cylinder and may comprise at least one arm 42. The arm 42 may be engaged in the recess or slot 32 of the proximal grip part 31 before the device is primed, inhibiting and/or restraining rotation of the rotatable part 40 relatively to the grip and blocking the locking mechanism.

When the device 10 is primed by screwing medicament container holder 13 into the grip, the upper end of threaded part 15 may push the arm 42 in the distal direction and disengage the arm 42 from the recess or slot 32 of the proximal grip part 31. Accordingly, when the device 10 is primed, the rotatable part 40 can be rotated as far as the plunger rod allows, for example a predetermined angle of 90 degrees.

The rotatable part 40 may further have at least one projection 41. The projection 41 preferably extends radially inwards from inner wall of the rotatable part 40. As shown in FIG. 5, the projection 41 preferably has the general shape of an arc of a circle. Furthermore, the rotatable part 40 may have at least one first slot 43, which preferably is provided in the wall portion of the rotatable part 40. Instead of or additional to slot 43, the rotatable part may comprise a recess, an indent or a second projection.

Figure 7:
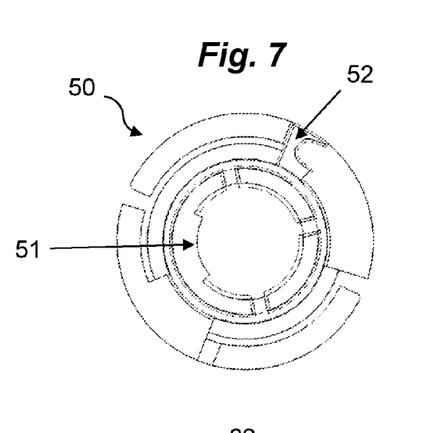
FIG. 7: Plan view showing a turning knob of a device for medicament delivery according to the present invention.
Figure 8:
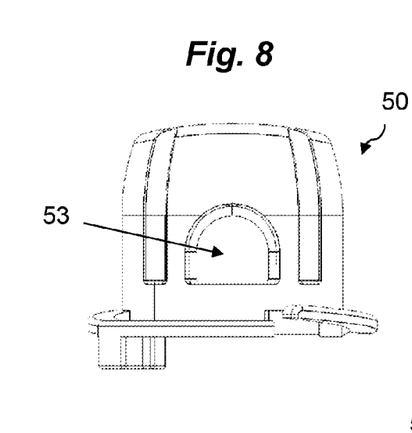
FIG. 8: Side view showing a turning knob of a device for medicament delivery according to the present invention.

FIGS. 7 and 8 show a plan view and a side view of a turning knob 50, which a device for medicament delivery 10 according to the present invention may comprise. The turning knob 50 preferably has the general shape of a hollow cylinder and may be provided with at least one first projection 51. The projection 51 may extend radially inwards from the wall of the turning knob 50 and preferably interacts or is in engagement with the at least one first slot 43 of the rotatable part 40. Preferably, the first projection 51 of the turning knob 50 extends radially inwards into the first slot 43 of the rotatable part 40. However, when the rotatable part 40 comprises a second projection instead of the first slot 43, the turning knob 50 may also have at least one recess engaged with the second projection of the rotatable part 40. The turning knob 51 preferably interacts or is engaged with the rotatable part 40 directly, such that the rotatable part 40 is rotated when the turning knob 50 is turned and that turning of the turning knob 50 is not possible when rotation of the rotatable part 40 is inhibited.

Figure 9:
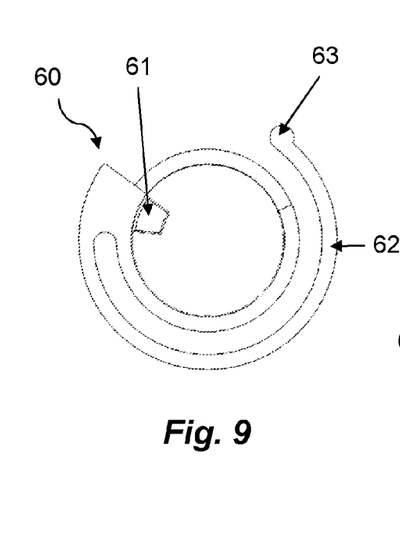
FIG. 9: Plan view showing an indicator drum of a device for medicament delivery according to the present invention.
Figure 10:
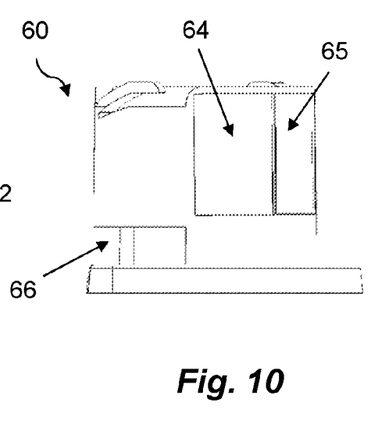
FIG. 10: Side view showing an indicator drum of a device for medicament delivery according to the present invention.

FIGS. 9 and 10 show a plan view and a side view of an indicator drum 60 of a device for medicament delivery 10 according to the present invention. The indicator drum 60 preferably has the general shape of a hollow cylinder and may feature at least one colour field. Preferably, two colour fields 64, 65 are disposed on the outer wall of the indicator drum. Depending on the position of the locking mechanism one of colour fields 64, 65 may be visible through at least one window 53 of the turning knob 51. The window 53 may also be a transparent segment. The colour fields 64, 65 may have different colours. For example, field 64 may be red and field 65 may be green.

The indicator drum may comprise at least one opening 66. Preferably, the at least one arm 42 of the rotatable part 40 extends through said opening 66.

Figure 11:
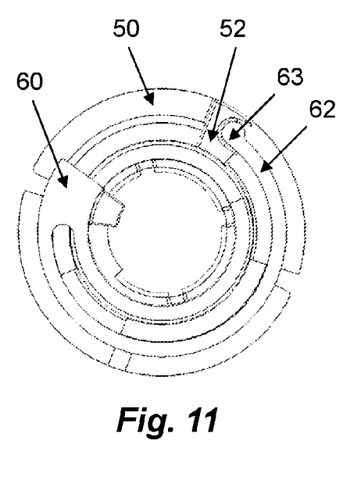
FIG. 11: Plan view showing an indicator drum and a turning knob of a device for medicament delivery according to the present invention, a resilient member of the indicator drum being engaged in a projection of the turning knob.

FIG. 11 shows a plan view of an indicator drum 60 being disposed within a turning knob 50. The indicator drum 60 preferably comprises a resilient member 62 with a head portion 63. The resilient member may be integral with the indicator drum. However, it will be clear to the person skilled in the art that the resilient member 62 may be a separated component. The resilient member 62 may be a separate component or integral with the turning knob 50 and/or the rotatable part 40. The resilient member 62 of the indicator drum preferably is a spiral spring. The indicator drum 60 preferably interacts or is in engagement with the turning knob 50 and/or the rotatable part 40 over the resilient member 62.

The turning knob 50 preferably comprises at least one second projection 52. As shown in FIG. 11, the head portion 63 of the resilient member 62 may be connected to the turning knob 50 while the other end is connected to or integral with the indicator drum 60. The head portion of the resilient member 62 may be held in the second projection 52 of the turning knob 50 by form closure. When the rotatable part and/or the turning knob is rotated, the end of the resilient member connected to the rotatable part or the turning knob will be rotated therewith.

Figure 13:
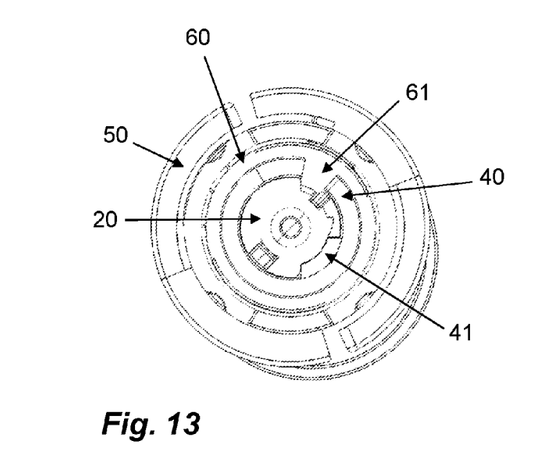
FIG. 13: Sectional view showing the locking mechanism of a device for medicament delivery according to the present invention in the ready position, the sectional plane being perpendicular to the longitudinal axis of the device and showing a projection of the rotatable part and a projection of the indicator drum interacting with grooves of the plunger rod.

As visible most clearly in FIG. 13, the rotatable part 40, the indicator drum 60 and the turning knob 50 preferably are substantially concentric with the plunger rod 20. More preferably the rotatable part 40 is disposed around the plunger rod 20, the indicator drum 60 is disposed around the rotatable part 40 and the turning knob 50 is disposed around the indicator drum 60.

Preferably, at least one projection 41 of the rotatable part 40 interacts or is in engagement with the steps of the channel 22 of the plunger rod 20 formed by parallel grooves 23 and perpendicular grooves 24. The steps preferably provide longitudinally and angularly offset abutment surfaces to the projection 41 of the rotatable part 40. When the locking mechanism 17 is in a locking position, the projection 41 of the rotatable part 40 abuts against an abutment surface 25 which is perpendicular to the longitudinal axis 29 of the plunger rod 20 (see FIG. 12). By rotating the rotatable part 40 and/or the turning knob 50 a predetermined angle, the projection 41 of the rotatable part 40 is slit along the perpendicular groove 24 until it reaches the next parallel groove 23 and abuts against an abutment surface 26 which is parallel to the longitudinal axis 29 of the plunger rod 20. The rotation of the rotatable part 40 thus preferably is substantially inhibited when it has been rotated for the predetermined angle. Detents 27 prevent the rotatable part 40 from being rotated backwards. The locking mechanism 17 is in a delivery position, i.e., released from locking (see FIG. 14), and the plunger rod 20 can be moved in the proximal direction until the projection 41 of the rotatable part 40 abuts against the next abutment surface 25 which is perpendicular to the longitudinal axis 29 of the plunger rod 20, thereby moving the plunger 16 along the medicament container 14 and ejecting and/or injecting a predetermined dose of the medicament contained therein. The locking mechanism 17 is in a locking position again. It will be clear to the person skilled in the art that abutment points or lines may be provided instead of surfaces 25, 26 and that projections may be provided on the plunger rod instead of grooves 23, 24.

The locking mechanism 17 preferably can be set to a delivery position again by rotating the rotatable part 40 and moving the plunger rod 20 in the proximal direction subsequently. Accordingly, multiple defined doses may be injected in an intermittent manner by iterating the steps of rotating the rotatable part 40 and pushing the plunger rod 20.

Figure 14:
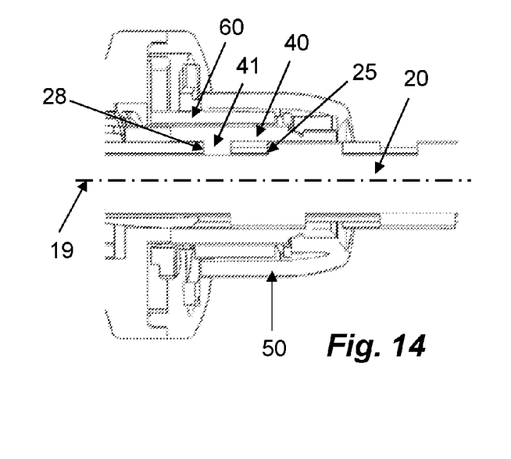
FIG. 14: Sectional view showing the locking mechanism of a device for medicament delivery according to the present invention in the ready position, the sectional plane being parallel to the longitudinal axis of the device and showing a projection of the rotatable part interacting with a groove of the plunger rod.
Figure 15:
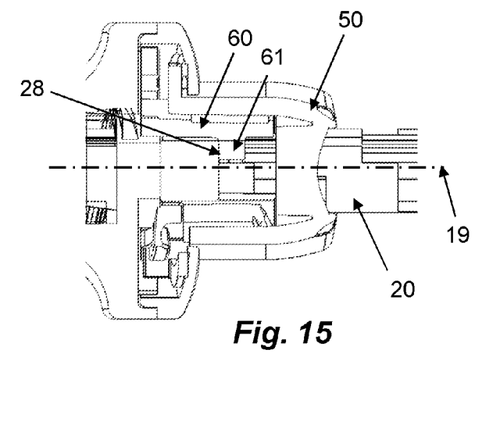
FIG. 15: Sectional view showing the locking mechanism of a device for medicament delivery according to the present invention in the ready position, the sectional plane being parallel to the longitudinal axis of the device and showing a projection of the indicator drum interacting with a groove of the plunger rod.

The indicator drum 60 preferably comprises at least one projection 61. Preferably, at least one projection 61 of the indicator drum 60 also interacts or is in engagement with the steps of the channel 22 of the plunger rod 20. When the locking mechanism 17 is in a locking position and/or a delivery position, the projection 61 of the indicator drum 60 preferably substantially inhibits movement of the plunger rod 20 in the distal direction (see FIG. 15) by abutting an abutment surface 28 which is perpendicular to the longitudinal axis 29 of the plunger rod 20 and faces towards the distal end of the plunger rod 20. Accordingly, the projection 61 of the indicator drum 60 preferably substantially inhibits the plunger rod 20 being pulled out of the device 10. The projection 61 of the indicator drum 60 and the projection 41 the rotatable part 40 interacting with the plunger rod 20 preferably are provided at different positions along the longitudinal axis 29 of the plunger rod 20 and/or at different angles of rotation around the longitudinal axis 29 of the plunger rod. FIGS. 14 and 15, which illustrate the locking mechanism 17 in the delivery position, show cross sectional planes that are angularly offset. While FIG. 14 shows the projection 41 of the rotatable part 40, FIG. 15 shows the projection 61 of the indicator drum 60. The projection 41 and the projection 61 are provided at different positions along and at different angles of the longitudinal axis 29 of the plunger rod 20.

When the locking mechanism is in a locking position and when the locking mechanism is set to a delivery position by rotating the rotatable part 40 and the turning knob 50, the rotation of the indicator drum 60 in a certain direction drum preferably is substantially inhibited by the projection 61 of the indicator drum 60 abutting against an abutment surface 26 which is parallel to the longitudinal axis 29 of the plunger rod 20. Therefore, the resilient member 62 connecting the indicator drum 60 with the turning knob 50 preferably is biased when the turning knob 50 and the rotatable part 40 are rotated for setting the locking mechanism 17 to a delivery position.

The rotation of the turning knob 50 relatively to the indicator drum 60 preferably leads to the device 10 indicating that the locking mechanism 17 is in a delivery position by switching the colour field visible through the window 53 of the turning knob 50. Preferably, the window of the turning knob 50 is disposed over a first colour field 64 when the locking mechanism 17 is in a locking position and over a second colour field 65 when the locking mechanism is in a delivery position. Detents 27 interact with the projection 41 and prevent the rotatable part 40 being rotated backwards.

When the plunger rod 20 is moved in the proximal direction the projection 61 slides along a parallel groove 23 until reaching a perpendicular groove 24. Then, the projection 61 does not abut with the abutment surface 26 anymore and is rotated due to the force exerted by the at least one biased resilient member 62 until reaching the next parallel groove 23 and abutting against an abutment surface of the at least one first slot 43 again. The indicator drum 60 is thus rotated in the direction into which rotation was previously inhibited and its position relatively to the turning knob 50 and the rotatable part 40 is reset. Rotation of the indicator drum 60 relatively to the turning knob 50 and the rotatable part 40 preferably leads to the colour field 65 shown through the window 53 of the turning knob 50 being reset to colour field 64. The next dose can be delivered by rotating the turning knob 50 again.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

Furthermore, in the claims the word "comprising" does not exclude other elements or steps, and the indefinite article "a" or "an" does not exclude a plurality. A single unit may fulfil the functions of several features recited in the claims. The terms "essentially", "about", "approximately" and the like in connection with an attribute or a value particularly also define exactly the attribute or exactly the value, respectively. Any reference signs in the claims should not be construed as limiting the scope.

The invention claimed is:

1. A device for medicament delivery with syringe-like usability, comprising:
   a grip, wherein the grip comprises separate proximal and distal grip parts with at least one projection;
   a medicament container holder that is movable toward the grip in a longitudinal direction of the device;
   a plunger rod that is substantially rotationally fixed relative to the grip by cooperating with the at least one projection, whereby the proximal and distal grip parts are rotationally fixed relative to each other;
   a rotatable part that is rotatable relative to the grip and that, when in a locking position, inhibits movement of the plunger rod in the longitudinal direction for dose delivery until being rotated; and
   a restraining member that restrains rotation of the rotatable part and abuts or connects to the rotatable part and the grip until the medicament container holder is moved toward the grip for interacting with the restraining member.

2. The device of claim 1, wherein the restraining member includes an arm.

3. The device of claim 2, wherein the arm is integral with the rotatable part.

4. The device of claim 2, wherein the arm restrains rotation of the rotatable part by engagement with a slot or projection of the grip.

5. The device of claim 1, wherein the restraining member is pushed or deflected by the medicament container holder when the medicament container holder is moved toward the grip.

6. The device of claim 1, wherein the medicament container holder is movable in the longitudinal direction by being screwed into the grip.

7. The device of claim 1, wherein the device is primed or contents of a medicament container are mixed when the medicament container holder is moved toward the grip.

8. The device of claim 7, wherein the medicament container has two chambers holding the contents that are mixed when the medicament container holder is moved toward the grip.

9. The device of claim 7, wherein the device de-airs the medicament container after the contents have been mixed.

10. The device of claim 1, wherein the rotatable part is substantially fixed in the longitudinal direction relative to the grip.

11. The device of claim 1, wherein a projection of the rotatable part interacts with a channel or a projection of the plunger rod.

12. The device of claim 1, wherein rotating the rotatable part relative to the plunger rod makes the device ready for actuation.

13. The device of claim 12, wherein the rotatable part is rotated by rotating a knob that interacts with the rotatable part.

14. The device of claim 1, further comprising an indicator drum that indicates a delivery position, in which the plunger rod is movable in the longitudinal direction relative to the grip for dose delivery, or a locking position.

15. The device of claim 14, wherein the indicator drum is connected to a knob or the rotatable part over a resilient member.

16. The device of claim 1, wherein the plunger rod has a plurality of steps provided in a threaded manner.

17. The device of claim 16, wherein the steps are formed by alternating parallel and perpendicular grooves or projections.

18. A device for medicament delivery with syringe-like usability, comprising:
   at least one grip, wherein the grip comprises separate proximal and distal grip parts having at least one projection;
   at least one medicament container holder; and
   at least one rotatable part which is rotatable relatively to a plunger rod and the grip and interacts with the grip to substantially inhibit movement of the plunger rod in a longitudinal direction for dose delivery when the plunger rod is in at least one locking position until being rotated;
   wherein the plunger rod is substantially rotationally fixed relative to the grip by cooperating with the at least one projection, whereby the proximal and distal grip parts are rotationally fixed relative to each other; the medicament container holder is movable toward the grip in the longitudinal direction of the device, and rotation of the rotatable part is restrained by at least one restraining member abutting or being connected to the rotatable part and the grip until the medicament container holder is moved toward the grip for interacting with the at least one restraining member.

* * * * *